(12) United States Patent
Herman et al.

(10) Patent No.: US 10,354,106 B2
(45) Date of Patent: Jul. 16, 2019

(54) ELECTRONICALLY READABLE DIETARY TAG AND READER

(71) Applicant: TUTSHO, LLC, Bellevue, WA (US)

(72) Inventors: Michele K. Herman, Bellevue, WA (US); William J. Herman, Bellevue, WA (US)

(73) Assignee: TUTSHO, LLC, Bellevue, WA (US)

( * ) Notice: Subject to any disclaimer, the term of this patent is extended or adjusted under 35 U.S.C. 154(b) by 158 days.

(21) Appl. No.: 14/766,866

(22) PCT Filed: Feb. 13, 2014

(86) PCT No.: PCT/US2014/016326
§ 371 (c)(1),
(2) Date: Aug. 10, 2015

(87) PCT Pub. No.: WO2014/127168
PCT Pub. Date: Aug. 21, 2014

(65) Prior Publication Data
US 2015/0379318 A1    Dec. 31, 2015

Related U.S. Application Data

(60) Provisional application No. 61/764,172, filed on Feb. 13, 2013.

(51) Int. Cl.
*G06F 7/00* (2006.01)
*G06F 17/30* (2006.01)
(Continued)

(52) U.S. Cl.
CPC ....... *G06K 7/10366* (2013.01); *G06F 16/242* (2019.01); *G06K 19/06037* (2013.01); *G06Q 10/10* (2013.01); *G06Q 50/24* (2013.01)

(58) Field of Classification Search
CPC ......... G06K 7/10366; G06K 19/06037; G06Q 10/10; G06Q 50/24; G06F 17/30389
(Continued)

(56) References Cited

U.S. PATENT DOCUMENTS

| 6,038,546 A | * | 3/2000 | Ferro | G06Q 30/06 705/15 |
| 8,418,915 B1 | * | 4/2013 | Miller | G06Q 30/06 235/375 |

(Continued)

FOREIGN PATENT DOCUMENTS

WO    WO 2010/019518 A1    2/2010

OTHER PUBLICATIONS

"Restaurants Menus and QR Codes", Jan. 2, 2012.*
(Continued)

*Primary Examiner* — Binh V Ho
(74) *Attorney, Agent, or Firm* — Thomas Horstemeyer, LLP

(57) ABSTRACT

The present invention relates to a programmable tag that is encoded with information associated with ingestible substances, a system for producing such a tag, and a reader for capturing and decoding the tag. Predetermined profiles and predetermined coding schemes are used to encode such information to form the tag and to decode and extract such information in accordance with the present invention.

4 Claims, 11 Drawing Sheets

(51) Int. Cl.
*G06K 7/10* (2006.01)
*G06F 16/242* (2019.01)
*G06Q 50/24* (2012.01)
*G06Q 10/10* (2012.01)
*G06K 19/06* (2006.01)

(58) Field of Classification Search
USPC .......................................................... 707/758
See application file for complete search history.

(56) References Cited

U.S. PATENT DOCUMENTS

| | | | | |
|---|---|---|---|---|
| 2002/0004749 | A1* | 1/2002 | Froseth | G06Q 10/08 705/16 |
| 2004/0006494 | A1* | 1/2004 | Badinelli | G06F 19/324 705/2 |
| 2004/0103043 | A1* | 5/2004 | Reade | G06Q 20/208 705/23 |
| 2006/0081711 | A1 | 4/2006 | Zhao et al. | |
| 2006/0244566 | A1* | 11/2006 | Sullivan | G06K 7/10336 340/10.1 |
| 2007/0088746 | A1* | 4/2007 | Baker | G06Q 30/0601 |
| 2008/0296380 | A1* | 12/2008 | Karkanias | G06Q 10/00 235/462.01 |
| 2010/0264205 | A1 | 10/2010 | Iida | |
| 2011/0301446 | A1* | 12/2011 | Kamen | A61M 5/14244 600/365 |
| 2012/0175413 | A1* | 7/2012 | Harris | G06K 19/06028 235/375 |
| 2013/0105565 | A1* | 5/2013 | Kamprath | G06F 19/3475 235/375 |
| 2014/0110468 | A1* | 4/2014 | Kandregula | G06Q 30/0241 235/375 |
| 2014/0114776 | A1* | 4/2014 | Solanki | G06Q 30/06 705/15 |
| 2014/0172531 | A1* | 6/2014 | Liberty | G06Q 20/3276 705/14.23 |
| 2017/0061418 | A1* | 3/2017 | Ferro | G06Q 30/02 |

OTHER PUBLICATIONS

"Netherlands Launch QR Code Nutritional Campaign On Large Scale"; CANI Communications; http://begrious.com/netherlands-launch-qr-code-nutritional-campaign-on-large-scale/; © 2015; accessed Mar. 9, 2015; 2 pages.
Canadian Patent Application 2,901,112 filed on Feb. 13, 2014, Notice of Allowance dated Mar. 23, 2017.
International Patent Application No. PCT/US2014/016326; Int'l Preliminary Report on Patentability; dated Aug. 27, 2015; 8 pages.
Assadi; "Healthy Eating QR-Code"; Presentation; 2014; 15 pages.
"QR Code Generator"; Nutrition Addition; http://www.nutritionaddition.com/extensions/qr-code-generator/; 2015; accessed Jul. 27, 2015; 1 page.
Richheimer; "SU dining halls add QR codes to provide nutritional information about food items"; The Daily Orange; http://dailyorange.com/2015/02/su-dininghalls-add-dr-codes-to-provided-nutritional-information-about-food-items./; 2015; accessed Jul. 27, 2015; 5 pages.
Strube; "Using QR Codes to Store Nutritional Information" UDI Coding Solution; http://franklinstrube.com/blog/using-qr-codes-to-store-nutritional-information/; Mar. 2010; accessed Jul. 27, 2015; 2 pages.
King; "Technology Aids University's Health Efforts"; Food Service Director; http://www.foodservicedirector.com/ideas-innovation/health-wealthness/articles/technology-aids-university-s-health-efforts; Mar. 2012; accessed Jul. 27, 2015; 2 pages.
Canadian Patent Application 2,901,112, Examiner Requisition dated Aug. 11, 2016.
Canadian Patent Application 2,901,112, Response to Examiner Requisition dated Aug. 11, 2016.
Canadian Patent Application 2,901,112, Claim Amendments as part of Response to Examiner Requisition dated Aug. 11, 2016.

* cited by examiner 202 204 206

202 204 206

FIG. 7A
```
                  SALE
   Product         Price    TUTSHO
   -----------------------------------
   Cheese Platter   7.00
   -----------------------------------
   Total            USD       7.00
   Amex             USD       7.00
   -----------------------------------
   Signature
```
FIG. 7B
Featured Products
  
NEW Fritos' Chicken Enchilada Melt        NEW Spicy Tuna        NEW Sriracha Steak Melt
  

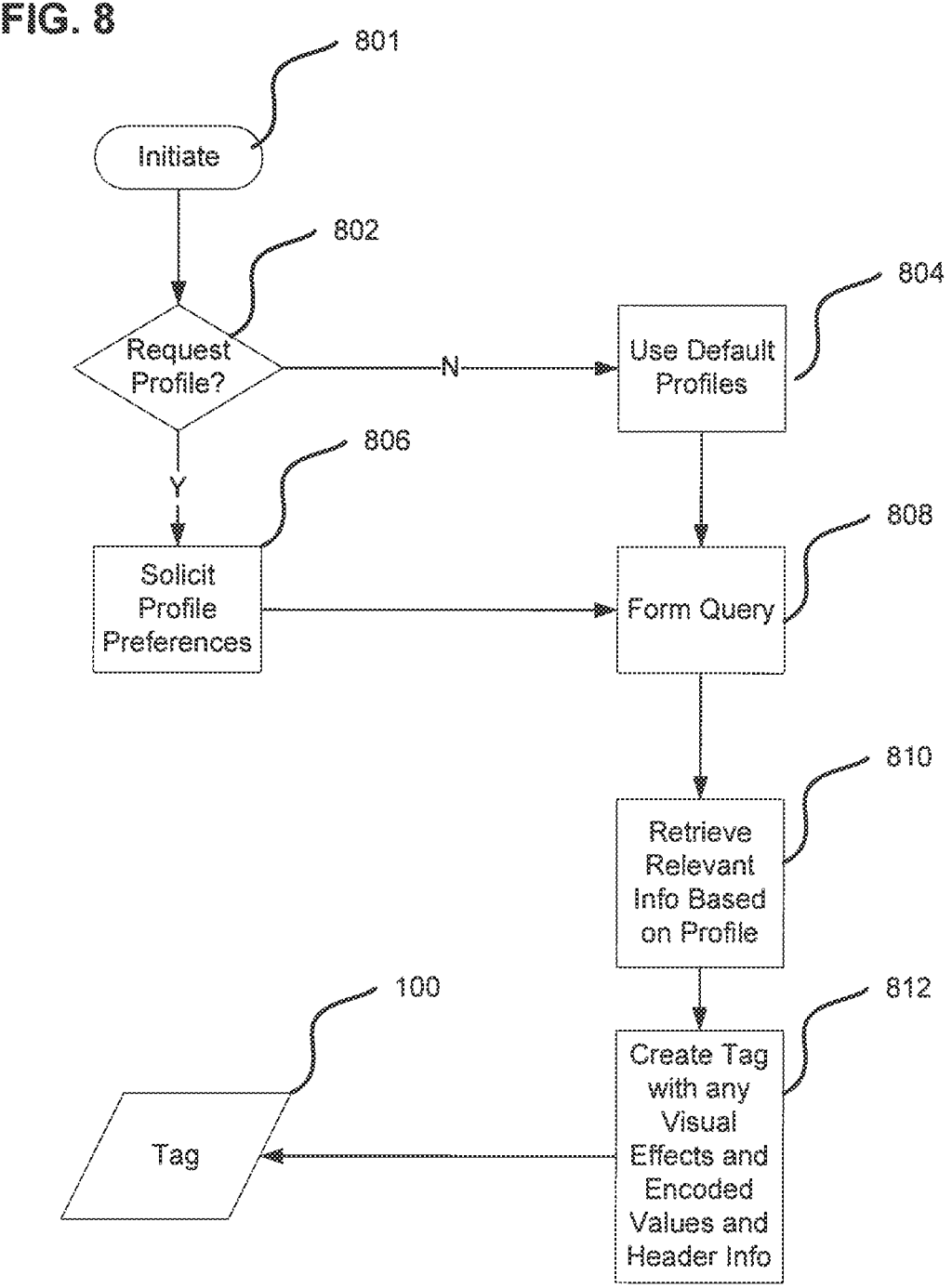

ELECTRONICALLY READABLE DIETARY TAG AND READER

CROSS REFERENCE TO RELATED APPLICATIONS

This application is a National Stage of International Application No. PCT/US2014/016326, filed Feb. 13, 2014, which claims the benefit of U.S. Provisional Patent Application No. 61/764,172, filed Feb. 13, 2013, the disclosures of which are incorporated herein by reference in their entireties.

TECHNICAL FIELD

This disclosure relates to food product labels, and computer readable labels.

BACKGROUND

Increasingly populations in the developed world, particularly the U.S., are battling obesity. In addition, many diseases, illnesses and the like are increasingly being linked to nutritional deficiencies. As a result, there is a need to track dietary consumption and adjust and maintain diets according to an individual's health needs. The challenge, however, is that it is very difficult for busy individuals, who do not have time to record everything they eat or drink, or that purchase made-to-order foods at a variety of venues (e.g., restaurants, booths at stadiums, street carts, kiosks, etc.), to track their diets and make appropriate choices and adjustments to their consumption.

There is similarly a need to easily identify allergens and other substances in consumable products to avoid harmful reactions that could be avoided.

SUMMARY

In recent years there has been a proliferation of mobile computers such as personal digital assistants (PDAs) and web-enabled cell phones. Some embodiments of the present invention address the need to track dietary consumption or other ingestible substances by taking advantage of the wide use of such PDAs. In sum, some embodiments of the present invention use a nutritional tag that is coded in accordance with a predetermined scheme. In a preferred embodiment the nutritional tag comprises a plurality of rows. Each row corresponds to a nutritional or dietary characteristic commonly found on a nutrition label. Such nutritional characteristics include but are not limited to calories, carbohydrates, fat, vitamins and minerals. In a preferred embodiment, the rows are populated with cells that when marked or unmarked are indicative of the value for the nutritional characteristic associated with the row. Those skilled in the art will recognize that other methods of coding the nutritional tag are feasible. According to an embodiment of the present invention the nutritional tag is printed on a receipt associated with the purchase of food or beverages, printed on a menu alongside each menu item, printed on labels affixed to products, displayed electronically on electronic menus or in e-receipts, or otherwise made available in a way that the nutritional tag can be read or identified and decoded using one's PDA (e.g., wired or wireless transmission of the tag information).

An embodiment of the present invention also comprises a tag reader that is capable of reading the nutritional tag in printed form or electronic form, or in any form that it may be received by the tag reader, a decoder for decoding the values associated with each of the nutritional characteristics, a database for storing the values, and an application for tabulating the amount of each nutritional characteristic the individual has consumed based on the values stored in the database. The application, according to a preferred embodiment of the invention, will generate an alarm if the individual's intake exceeds predetermined thresholds set by the individual. In another embodiment, the application can review food and beverage choices in advance and suggest other alternatives that may be available at, for example, the same store or restaurant that will not cause the thresholds to be exceeded.

The present invention may also include an interface to analysis tools that may be utilized by the individual, his or healthcare provider, trainer, coach, or the like to set thresholds and generate preferences that can be used by the application to seek appropriate food and beverage selections for the individual based on the availability of such products at a given venue.

The tag may also be used to code other types of information associated with ingestible substances such as allergens or drug directive information.

BRIEF DESCRIPTION OF THE DRAWINGS

The foregoing summary as well as the following detailed description are better understood when read in conjunction with the appended drawings. For the purpose of illustrating the invention, there is shown in the drawings exemplary constructions of the invention; however, the invention is not limited to the specific methods and instrumentalities disclosed.

FIGS. 7A and 7B show examples of a tag printed on a receipt and menu, respectively.

FIG. 8 shows a process of producing a tag according to one embodiment of the present invention.

DETAILED DESCRIPTION OF ILLUSTRATIVE EMBODIMENTS

Figure 1:
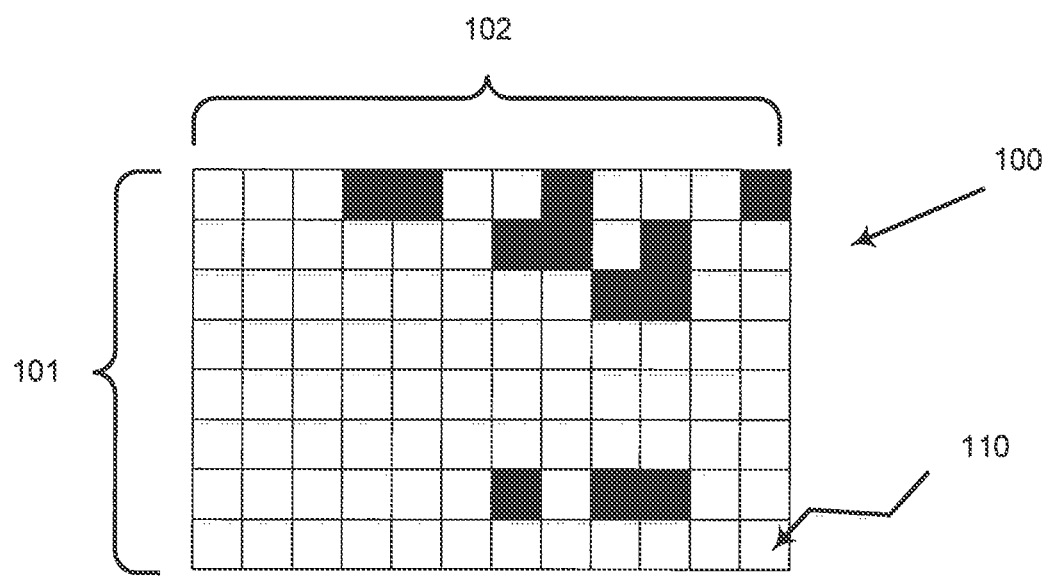
FIG. 1 shows a nutritional tag in accordance with one embodiment of the present invention.

A nutritional tag 100 is shown in FIG. 1. A plurality of rows 101 and columns 102 form a number of cells 110. The rows or columns form fields associated with a nutritional characteristic such as calories, fat, carbohydrates, vitamins or minerals. It should be understood that such fields may be representative of other ingestible substances such as allergens, drugs, chemicals and other ingredients that may be found in ingestible substances. The term nutritional characteristic as used herein is intended to include any such ingestible substances. Although the fields of tag 100 may be arranged by rows or columns, for purposes of simplified description, the fields may be described herein as arranged by rows only.

The nutritional characteristics associated with each field will be ordered in accordance with a predetermined scheme. For illustrative purposes only, a standard could be developed to specify multiple profiles. In accordance with this example only, a first profile could specify the following:

TABLE 1

| Row 101 Number | Nutritional Field | Unit of Measurement |
|---|---|---|
| 1 | Calories | Calories |
| 2 | Calories From Fat | Calories |
| 3 | Total Fat | Grams |
| 4 | Saturated Fat | Grams |
| 5 | Trans Fat | Grams |
| 6 | Cholesterol | Milligrams |
| 7 | Sodium | Milligrams |
| 8 | Total Carbohydrates | Grams |
| 9 | Dietary Fiber | Grams |
| 10 | Sugars | Grams |
| 11 | Protein | Grams |

In this example, the tag 100 would comprise 11 rows 101 and each row would be coded in accordance with the value associated with a food, beverage or other ingestible substance. In a preferred embodiment the coding is represented in Binary Coded Decimal. However, those skilled in the art will recognize that other coding schemes are also suitable, such as binary, or 2D matrix bar codes such as Aztec and the like. The profile would also have a predetermined serving size associated with the nutritional information. The serving size could be a specific measure or amount such as 1 tablespoon, ½ cup, or 6 ounces. Alternatively, the serving size could be equivalent to a single serving as sold for prepared, packaged, or ordered products. It should be understood that that the serving size may also be encoded into the tag rather than associated in a predetermined manner with a particular profile. For illustrative purposes only, a serving of Ricotta cheese could be specified as ¼ of a cup and have the following values associated with the profile specified in Table 1 above.

TABLE 2

| Row 101 Number | Nutritional Field | Unit of Measurement | Value |
|---|---|---|---|
| 1 | Calories | Calories | 90 |
| 2 | Calories From Fat | Calories | 5 |
| 3 | Total Fat | Grams | 6 |
| 4 | Saturated Fat | Grams | 3.5 |
| 5 | Trans Fat | Grams | 0 |
| 6 | Cholesterol | Milligrams | 30 |
| 7 | Sodium | Milligrams | 85 |
| 8 | Total Carbohydrates | Grams | 4 |
| 9 | Dietary Fiber | Grams | 0 |
| 10 | Sugars | Grams | 3 |
| 11 | Protein | Grams | 6 |

Figure 2A:
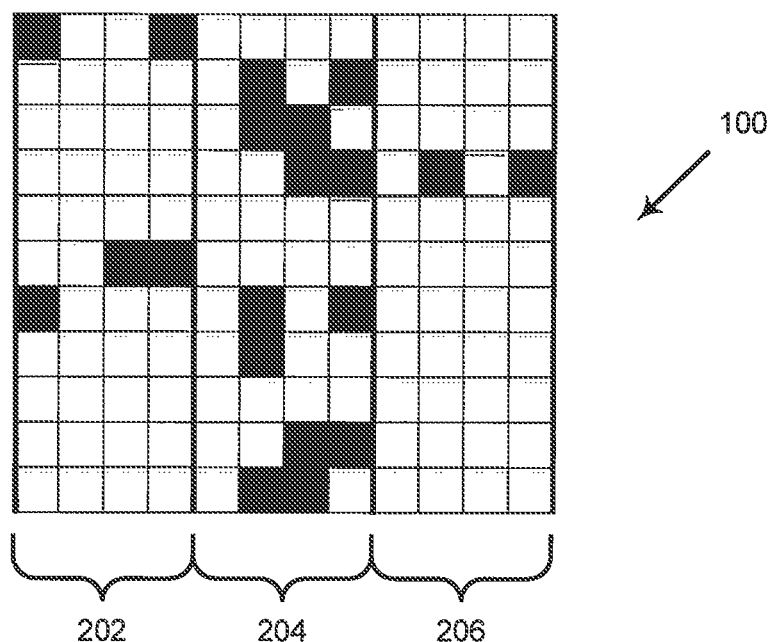
FIG. 2A shows an exemplary tag using BCD coding according to one possible predetermined profile.

The tag 100 for the above example of Ricotta cheese using BCD coding is shown in FIG. 2A. In the same example, the first 4 columns 202 represent the 10s digit of the value, the second 4 columns 204 represent the 1s digit of the value and the third 4 columns 206 represent the first decimal of the value. The number of 4-column sections 202, 204 and 206 should also be predetermined for each profile and may vary based on the values expected to be coded, i.e., whether or not decimal places are represented and/or whether a 100s or greater digits should be represented.

In a second profile according to the present example, the nutritional information may be extended as specified in Table 3 below.

TABLE 3

| Row 101 Number | Nutritional Field | Unit of Measurement |
|---|---|---|
| 1 | Calories | Calories |
| 2 | Calories From Fat | Calories |
| 3 | Total Fat | Grams |
| 4 | Saturated Fat | Grams |
| 5 | Trans Fat | Grams |
| 6 | Cholesterol | Milligrams |
| 7 | Sodium | Milligrams |
| 8 | Total Carbohydrates | Grams |
| 9 | Dietary Fiber | Grams |
| 10 | Sugars | Grams |
| 11 | Protein | Grams |
| 12 | Vitamin A | Percent of a 2,000 calorie diet |
| 13 | Calcium | Percent of a 2,000 calorie diet |
| 14 | Vitamin C | Percent of a 2,000 calorie diet |
| 15 | Iron | Percent of a 2,000 calorie diet |

For a serving of ricotta cheese, the values associated with the extended profile are listed in Table 4.

TABLE 4

| Row 101 Number | Nutritional Field | Unit of Measurement | Value |
|---|---|---|---|
| 1 | Calories | Calories | 90 |
| 2 | Calories From Fat | Calories | 5 |
| 3 | Total Fat | Grams | 6 |
| 4 | Saturated Fat | Grams | 3.5 |
| 5 | Trans Fat | Grams | 0 |
| 6 | Cholesterol | Milligrams | 30 |
| 7 | Sodium | Milligrams | 85 |
| 8 | Total Carbohydrates | Grams | 4 |
| 9 | Dietary Fiber | Grams | 0 |
| 10 | Sugars | Grams | 3 |
| 11 | Protein | Grams | 6 |
| 12 | Vitamin A | Percent of a 2,000 calorie diet | 4 |
| 13 | Calcium | Percent of a 2,000 calorie diet | 10 |
| 14 | Vitamin C | Percent of a 2,000 calorie diet | 0 |
| 15 | Iron | Percent of a 2,000 calorie diet | 0 |

Figure 2B:
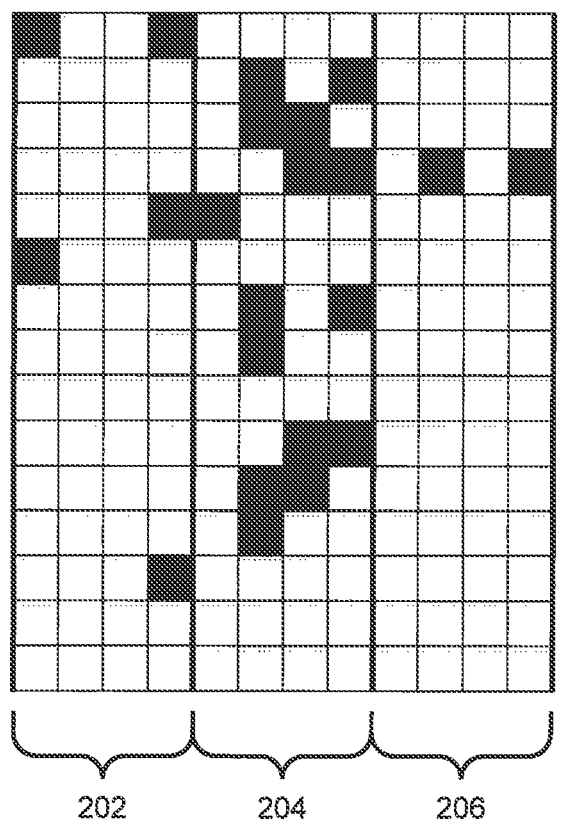
FIG. 2B shows an exemplary tag using BCD coding according to a second possible predetermined profile.

The tag 100 coded according to the extended profile for a serving of ricotta cheese is shown in FIG. 2B.

Figure 3A:
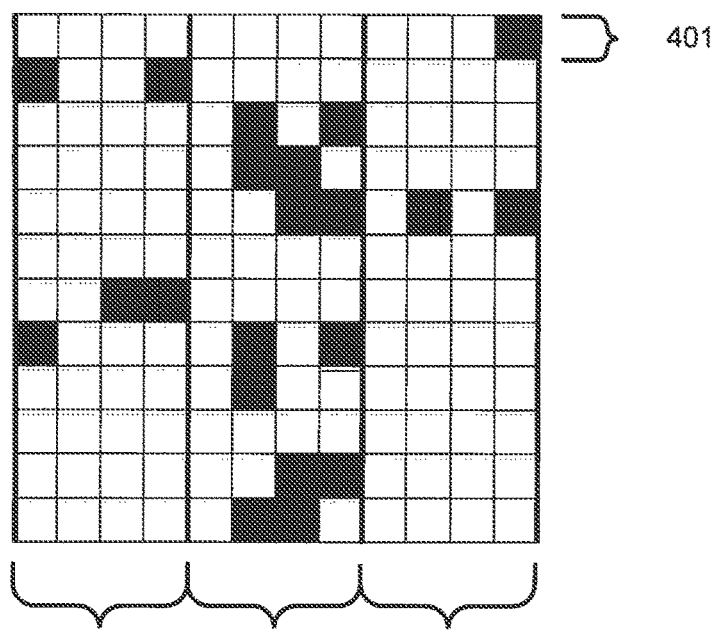
FIG. 3A shows the exemplary tag in FIG. 2A with a header representative of the predetermined profile in the example shown.
Figure 3B:
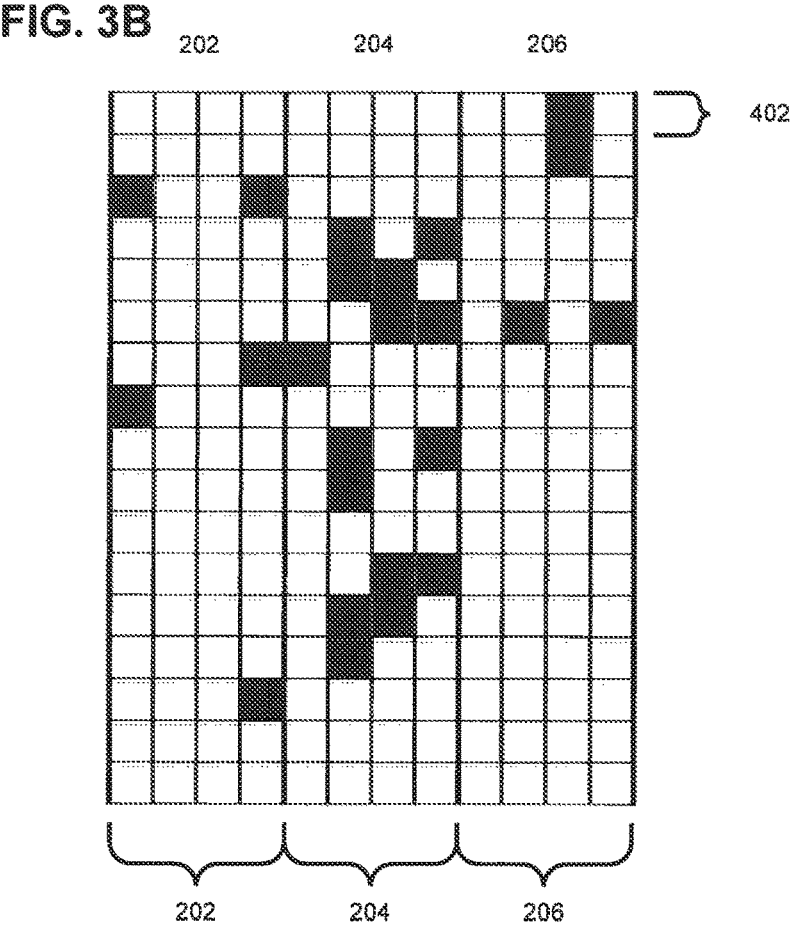
FIG. 3B shows the exemplary tag in FIG. 2B with a header representative of the predetermined profile in the example shown.

Differentiation among profiles may be implemented in a variety of ways. One way would be to include a header in the same coding format that would specify the profile. For example, suppose the profile shown in Table 1 above is identified as Profile 1 and the profile shown in Table 3 above is identified as Profile 2. In the example where BCD coding is used, the servings of ricotta cheese with the values represented in Tables 2 and 4, respectively would be shown in corresponding FIGS. 3A and 3B. Note that the first row 401 in FIG. 3A and 402 in FIG. 3B represents the header encoded with the applicable profile number.

Figure 4A:
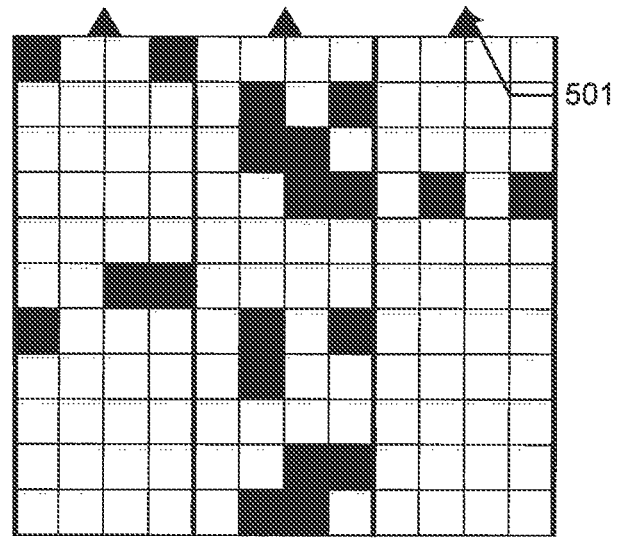
FIG. 4A shows the exemplary tag in FIG. 2A with visual effects representative of the predetermined profile in the example shown.
Figure 4B:
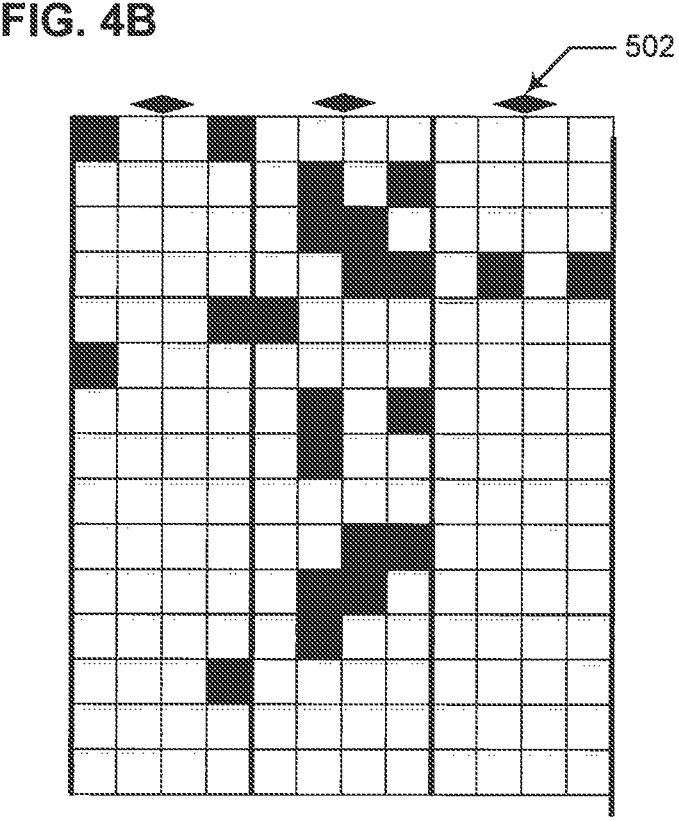
FIG. 4B shows the exemplary tag in FIG. 2B with visual effects representative of the predetermined profile in the example shown.

In an alternative embodiment, the profile identifier may be represented by visual or coded effects associated with the tag in a predetermined manner. For example, FIGS. 4A and 4B show Profiles 1 and 2 corresponding to a serving of ricotta cheese, respectively as described above using an exemplary visual effect. The small triangles 501 interspersed equidistantly across the top of the tag 100 in FIG. 4A is a possible predetermined way to identify Profile 1 and the small diamonds 502 interspersed equidistantly across the top of tag 100 in FIG. 4B is a possible predetermined way to identify Profile 2. It should be understood that many other effects are possible including but not limited to different designs, shapes, coloring of the cells, border designs and the like.

Figure 4C:
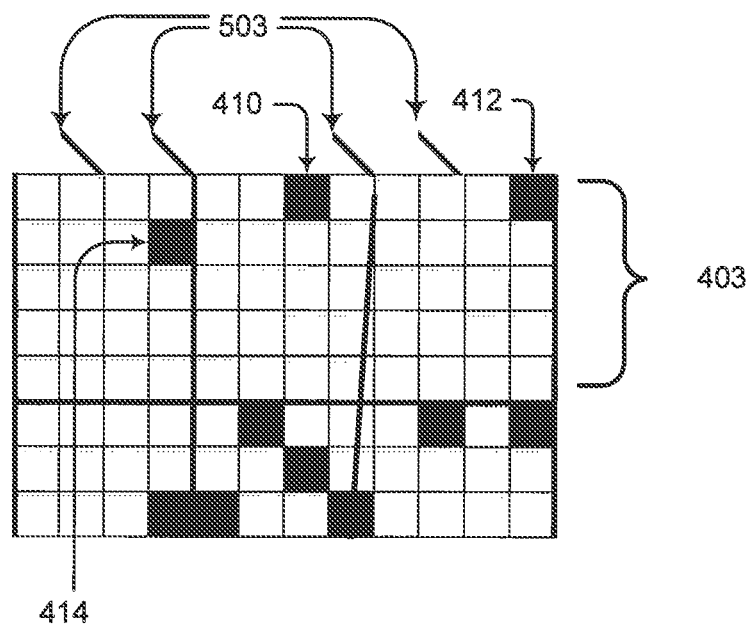
FIG. 4C shows an exemplary tag having both a header and visual effects to identify a third predetermined profile.

It should also be understood that some profiles may take advantage of both a header and a visual or coded effect to identify the profile represented. For example, a standard for all nutritional information could be created where the nutritional information would be listed in a predetermined order corresponding to a row number in a given tag. In creating the tag, only those rows to be tracked are included in the tag. The header for such tag would include a list of the row numbers corresponding to the nutritional information included in the tag. For instance, if an individual was interested in tracking only his niacin, calcium and Vitamin D intake, and the rows corresponding to niacin, calcium and Vitamin D are 7, 12 and 16 out of a possible 56 total predetermined rows, then the header could be represented as 56 cells with the 7th, 12th and 16th cell marked. A profile could be defined for this type of tagging, i.e., a subset of the universal list and identified by a visual effect. FIG. 4C shows an example of a tag 100 according to the foregoing description of a blended header and visual effect to identify the profile and information included in the tag where the header 403 specifies that niacin 410, calcium 412 and Vitamin D 414 are included and visual effect 503 specifies the blended profile.

Many profile variations are also contemplated by the present invention such as drug directives, allergens, artificial substances and the like. For example, a profile could also be created that specifies allergens or other substances to be avoided that are present in a particular ingestible substance. Table 5 shows an exemplary predetermined scheme for allergens and other substances that may be found in ingestible products that individuals may choose to avoid.

TABLE 5

| Row 101 number | Allergen |
| --- | --- |
| 1 | Gluten |
| 2 | Nuts |
| 3 | Dairy |

TABLE 5-continued

| Row 101 number | Allergen |
| --- | --- |
| 4 | Eggs |
| 5 | Aspartame |
| ... | ... |
| N | Caffeine |

Figure 5A:
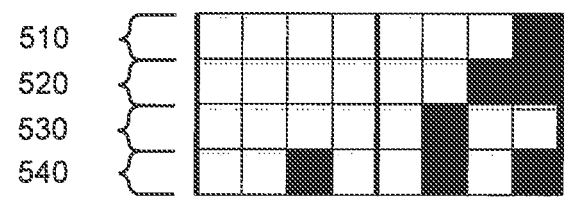
FIG. 5A shows an exemplary tag having an allergen profile.

The predetermined scheme may include N substances although very few ingestible substances would likely contain more than a fraction of such substances. Therefore, the tag associated with such a profile might include only the row numbers for those allergens or other substances that are present in a particular food. For example, a serving of chocolate cake may include gluten, dairy, eggs and caffeine. Assume for the purposes of this example that N=25. FIG. 5A shows a possible tag coded in BCD format for such a profile using the predetermined scheme in Table 5 for this serving of cake where the rows 510, 520, 530 and 540 represent the applicable row numbers in Table 5. Those skilled in the art will appreciate other methods of encoding such information are possible including the profiling and headers described above.

In the case of drug directives, a profile could be created for each drug with the relevant directives such as avoiding dairy or alcohol. Table 6 is an exemplary profile associated with drug directives.

TABLE 6

| Row 101 number | Drug Directives |
| --- | --- |
| 1 | Avoid dairy |
| 2 | Avoid excessive sunlight |
| 3 | Avoid operating heavy machinery such as driving a vehicle |
| 4 | Take with plenty of water |
| 5 | Take with food |
| ... | ... |
| N | Avoid alcohol |

Figure 5B:
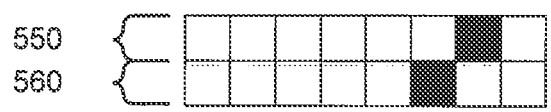
FIG. 5B shows an exemplary tag having a drug directive profile.

FIG. 5B shows an exemplary tag according to the profile shown in Table 6 for a hypothetical drug which should be taken with plenty of water and where the patient should avoid excessive sunlight. Using the same coding scheme as described above for the allergen profile, only the row numbers 2 and 4 would need to be represented in connection with this hypothetical drug. Assuming for this example that N=18 and BCD coding is used, FIG. 5B shows an exemplary tag for this drug directive profile for the same hypothetical drug. Row 550 represents the directive associated with avoiding excessive sunlight and row 560 represents the directive associated with taking the drug with plenty of water.

Figure 6:
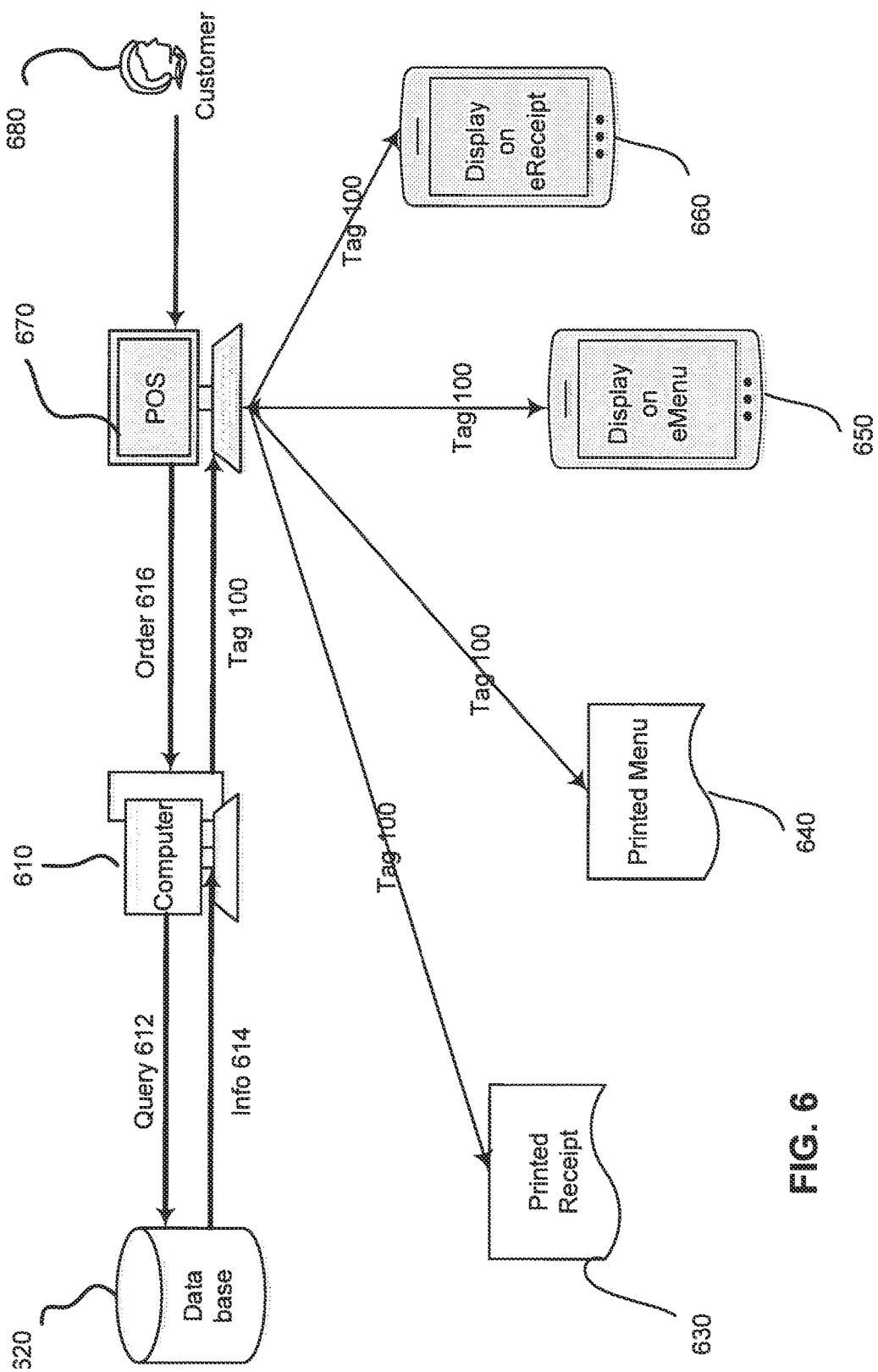
FIG. 6 shows a tagging system in accordance with one embodiment of the present invention in connection with a customer purchase.

FIG. 6 shows a tagging system in accordance with an embodiment of the present invention in connection with a customer purchase. As shown, a computer 610 queries a database 620 for the nutritional information needed to create a particular tag 100. The database 620 stores the names of the ingestible substance and any corresponding nutritional information, allergens or other characteristics relevant to the ingestible substance that might be included in a tag. For example, suppose a coffee shop with numerous shop locations chooses to produce tags for its customers. The corresponding database 620 would have a list of all of the different coffee drinks, baked goods, fruit, nutrition bars and anything else that the coffee shop sells. In one embodiment of the invention, a customer 680 in this example would order a 16 oz. hazelnut latte and a blueberry muffin from a point of sale (POS) terminal 670. The POS terminal 670 may include the computer 610 or it may be interfaced to a computer 610 as would be understood by those skilled in the art. The computer 610 receives the order 616 from the POS terminal 670 and forms a query 612 requesting information about a 16 oz. hazelnut latte and a blueberry muffin in accordance with one or more pre-programmed profiles, e.g., Profile 1 described above. The database 620 would retrieve the relevant information 614 and transmit such information 614 back to the computer 610 and the computer 610 would then proceed to assemble the information received to form a tag 100 in accordance with the relevant profile including the creation of any requisite header or visual effects. In one embodiment of the invention, the POS terminal 680 would print the tag 100 for each item purchased on a printed receipt 630 or on an electronic receipt 660. In a more preferred embodiment of the invention, the customer may also select which profile or profiles he or she is interested in so that the tag 100 is assembled in a customized manner for each customer. The query 612 would be tailored for the profile or profiles the customer requests.

In accordance with another aspect of the present invention, the tag 100 may be printed alongside the relevant menu item on a printed menu 640 or be made available in connection with a menu item on an electronic menu 650 which may be accessed by the customer at the point of sale, e.g., the coffee shop, or remotely at another time from any internet-enable device. In the case of an electronic menu, a customer may be provided with an interface to the computer 610 as described below whereby the customer is prompted to enter a particular profile of interest. The tags generated for the electronic menu will be representative of the profile selected by the customer.

FIGS. 7A and 7B show examples of a tag 100 printed on a receipt and menu, respectively.

FIG. 8 shows a process of producing a tag according to an embodiment of the present invention. The process may be initiated by a customer at a POS terminal as described above, or by a retailer that wants to label the ingestible substances it sells, a producer of ingestible products, a person or entity that distributes recipes, or anyone else interested in generating a tag. The process is initiated at 801 as an input identifying a specific food, beverage or other ingestible substance. In a preferred embodiment, profile information may be requested at 802. If profile information may be supplied, such information is requested at 806 or if it is not solicited, or may not be solicited, a default profile or profiles provided at 804 are used to form a query at 808 requesting the information for the specific, food, beverage or ingestible substance. The query is used to retrieve the relevant information based on the specific profile and food, beverage or other ingestible substance at 810. For example, if Profile 1 was specified for a serving of ricotta cheese, the information shown in Table 2 would be retrieved. The retrieved information is then encoded into a tag using a predetermined coding scheme as described above and the appropriate header and/or visual effects are generated according to a predetermined scheme as also discussed above and combined with the encoded information to form the tag at 812. The tag 100 is then output and can be printed or posted as described in connection with FIG. 6. It should be understood that the tag may also be communicated directly to an individual's tracking device, via wireless or wired connections, printed on a recipe, adhesively attached to an item such as produce or prepared sandwiches, and other means of associating the tag with a specific food, beverage or ingestible substance.

Figure 9:
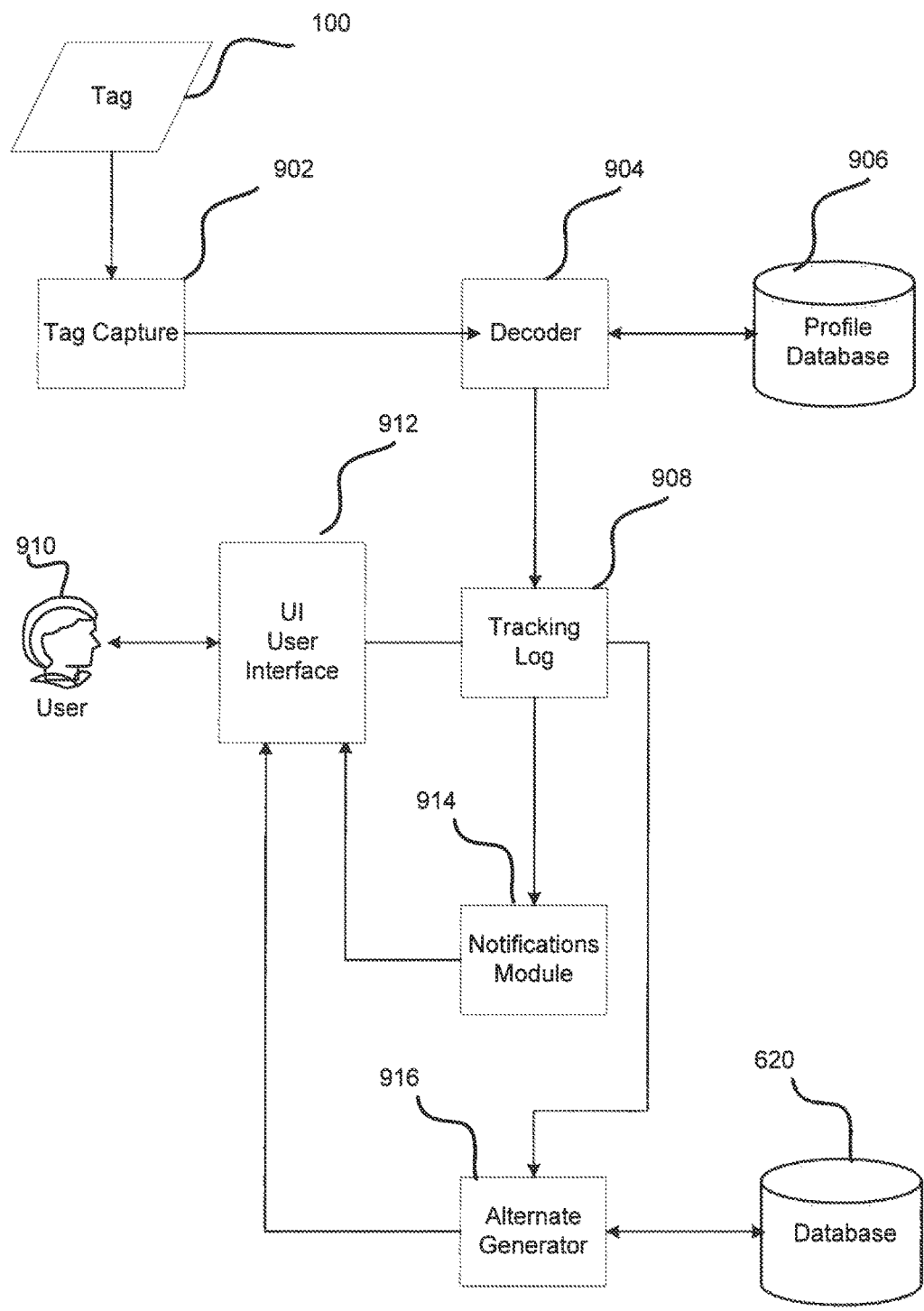
FIG. 9 shows a system for reading a tag according to one embodiment of the present invention.

FIG. 9 shows a system for reading a tag according to one embodiment of the invention. A tag capture device 902 may comprise an application that is programmed to read a tag 100. For example, the application could run on a PDA and scan a printed tag 100 in the manner a bar code or QR code reader running on a PDA is used to scan those types of codes to capture the code image. Alternatively, the tag 100 could be captured by selecting the tag from a website or an e-receipt displayed on a PDA or other computing device. It should also be understood that the present invention can provide means to transmit a tag from a POS terminal or other device to the tag capture device 902 such as a PDA, for example, using a Bluetooth or Wi-Fi connection. Once the tag is captured, a decoder 904 is used to first decode the header and/or visual effects to identify the profile associated with the scanned tag. According to one embodiment of the present invention, the predetermined profiles are stored in a profile database 906 that can be accessed by the decoder 904. The profile database 906 may be located on a remote server, on the consumer's local device, or anywhere that the consumer's local device, e.g., the PDA, may connect and access the database. The profile database 906 preferably includes all of the predetermined profiles (e.g., Tables 1, 3, and 5 above) and the header and/or visual effects associated with each. The decoder 904 matches the header and/or visual effects associated with the scanned tag to a profile in the profile database 906. The decoder 904 then reads the predetermined fields of the relevant profile from the profile database 906. The fields of the scanned tag are then decoded by decoder 906 according to a pre-programmed coding scheme, e.g., BCD, which corresponds to the predetermined coding scheme used to code the tags as described above. The values for each field decoded in the scanned tag are associated with the corresponding field description based on the profile information contained in the profile database 906.

In a preferred embodiment of the inventive nutritional tag, the values for each scanned tag are summed in a tracking log 908. For example, if a consumer scans a tag for his breakfast sandwich and decodes the tag such that the calorie field in the decoded profile yields 450 calories and then the consumer scans and decodes the tag for his orange juice such that the calorie field for the decoded profile yields 250 calories, the tracking log 908 would store each value in a log along with the cumulative value, in this example 700 calories as follows.

TABLE 7

| Substance | Serving Size or portion | Calories |
| --- | --- | --- |
| Breakfast Sandwich | 1 | 450 |
| Orange Juice | 1 | 250 |
| Total | | 700 |

Preferably the food, beverage or ingestible substance along with the serving size or portion is also logged with its corresponding entry as shown in Table 7 in the tracking log 908. Those skilled in the art will understand that there are numerous ways to supply the name or designation of a food, beverage or other ingestible substance, as well as the serving size or portion, and associate the same with the decoded and logged values such as, without limitation, entry by a consumer, a communication from the POS, selection from an electronic menu, encoding included with the tag, separate bar code identifiers, and the like.

In a more preferred embodiment, a user 910 such as a consumer, health professional, or trainer may select which information to track and any notifications or thresholds he or she may want to set. The user 910 communicates through a user interface (UI) 912 with the tracking log 908. It should be understand that the UI 912 may be provided by an application running on a device such as a PDA or another internet-enabled or wireless computing device and may accordingly be located locally with the tracking log 908 or could be located remote from the tracking log 908. To illustrate one scenario according to the invention, the user 910 may be provided with an input menu of nutritional characteristics he or she wants to track and the value limits not to be exceeded. The tracking log 908 uses such value limits to compare the cumulative values for the respective selected nutritional characteristics, and if a value limit is exceeded, the tracking log 908 will trigger the notification 914 to notify the user 910 through the UI 912 that the value limit has been exceeded. In a preferred embodiment of the invention the information logged such as the information listed in Table 7 is accessible to the user 910 on a local and/or remote computing device.

In another embodiment, the user 910 may specify or the tracking log 908 may be pre-programmed to initiate a search for alternatives foods or beverages available at the current venue that will not cause the value limits to be exceeded. In this embodiment of the invention, once the tracking log determines that a value has been exceeded, the tracking log 908 initiates a request communicated to the alternate generator 916 to search for a more suitable alternative food or beverage that does not exceed the relevant value limit. The alternate generator 916 queries the database 620 that was described in detail in connection with FIG. 6 to identify alternative choices that will not cause the value limit to be exceeded. Alternatives are then communicated to the user 910 through the UI 912. If no alternatives are identified then the alternate generator 916 communicates the same to the user 910. The user 910 may direct the tracking log 908 to replace the last entry logged that exceeded one or more value limits with an alternative selected by the user through the UI 912. It should be understood, that if other profiles related to, for example, allergens or drug directives, are selected by the user 910, then the value limits and notifications could be based on the presence of certain allergens in the case of an allergen-related profile or time-appropriate instructions in the case of a drug directive-related profile.

Figure 10:
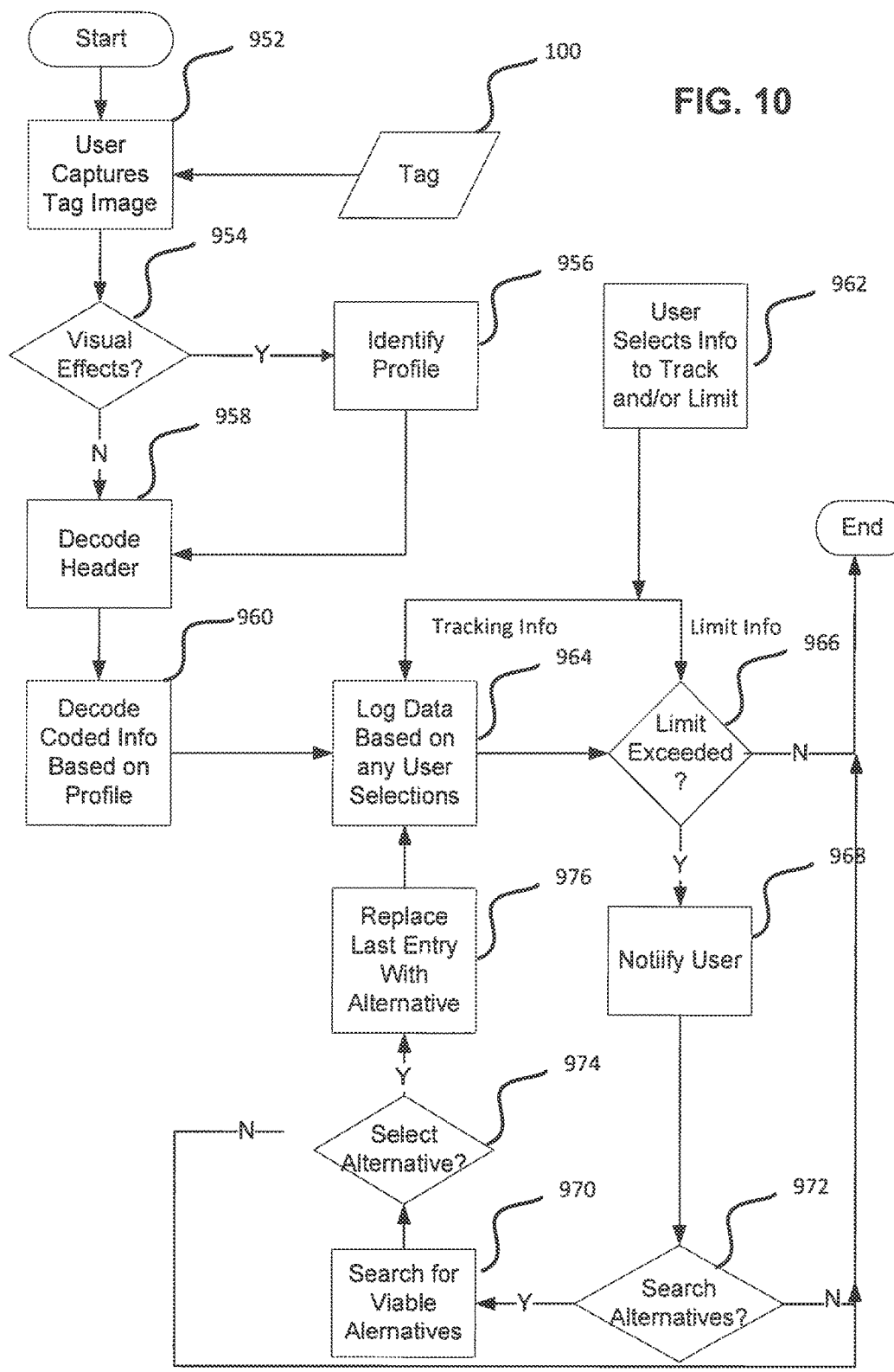
FIG. 10 shows a process for reading a tag according to one embodiment of the present invention.

FIG. 10 shows a process for reading a tag according to one embodiment of the present invention. A customer or user captures the tag at 952 in a manner described in detail above. The image of the tag is next analyzed at 954 to determine whether it contains any of the visual effects that are indicative of a particular predetermined profile. If such visual effects are detected, the corresponding profile is identified and used to decode the tag header at 958. As discussed above, some profiles may not rely on any visual effects and in such instances the header will be decoded at 958 in a manner corresponding to the predetermined header definition. Once the header and profile are known, the coded information contained in the tag is decoded at 960 to extract the relevant information such as the nutritional values, allergens, drug directives, and the like. For illustrative purposes only, the present process is described in connection with a tag containing nutritional information. The nutritional information decoded and extracted from the tag is logged at 964. Preferably each ingestible item that is logged individually along with the nutritional values associated with such ingestible item as discussed above. A total amount representative of the cumulative values for each nutritional characteristic to be tracked is also preferably logged at 964.

In a more preferred embodiment, the user also selects the nutritional information and the value limits for such nutritional characteristics at 962. In this preferred embodiment of the invention, only those nutritional values associated with the selected nutritional characteristics are logged and accumulated at 964. Further, the accumulated values are compared at 966 to any value limits supplied by the user to determine if such value limits have been exceeded by the cumulative value following the last logged entry. If a value limit is exceeded at 966, the user is notified at 968. If the value limit is not exceeded, the process ends and restarts upon the next tag capture at 952. In a further preferred embodiment, a search is made at 970 for alternatives available at the current venue that do not result in a value limit being exceeded. The process according to this embodiment of the invention prompts the user as to whether or not to perform the search for alternatives. If the user chooses to search for alternatives, such alternatives are identified at 970 and presented to the user. In an alternative embodiment, the tag reader is pre-programmed to automatically search for alternatives at 972 and 970. If an alternative is selected at 974 by the user, then the values for the last entry in the tracking log is replaced at 976 with the values associated with the selected alternative and a new cumulative set of values are logged at 964. If no alternative is selected at 974, the process ends and restarts upon the next tag capture at 952.

What is claimed:

1. A system for generating machine readable nutritional tags encoding nutritional information, comprising:

a database storing dietary product descriptions and associated nutritional values for various dietary products, wherein each nutritional value has a corresponding nutritional field and unit of measurement, each dietary product is associated with more than one set of dietary product descriptions and associated nutritional values, and each set is associated with a predetermined coding profile representative of an order of the nutritional fields and the corresponding units of measurement; and a computer coupled to the database and configured to generate a nutritional tag representing one set of the dietary product descriptions and associated nutritional values based upon the predetermined coding profile associated with the set, wherein the nutritional tag comprises at least one of a header and visual effects indicative of the predetermined coding profile a tag capture device configured to electronically read the nutritional tag;

a profile database for storing the predetermined coding profiles; and a decoder coupled to the tag capture device and the profile database to decode (i) the header or visual effects included in the nutritional tag to identify the predetermined coding profile stored in the profile database, and (ii) the nutritional tag to generate the subset of the dietary product descriptions and associated nutritional values based upon the predetermined coding profile.

2. The system of claim 1, further comprising:

a point of sale (POS) terminal coupled to the computer and configured to make a selected nutritional tag available to a consumer of a selected dietary product, wherein the selected nutritional tag is generated based on a specific dietary product description and associated nutritional information for the selected dietary product; and wherein the computer is configured to receive order information from the POS terminal and form a query requesting information from the database based on the order, and wherein the database is configured to respond to the query by retrieving relevant information and transmitting the relevant information to the computer, and the computer is further configured to proceed to use the information received from the database to form the selected nutritional tag, and wherein the POS terminal is further configured to print the selected nutritional tag on at least one of a printed receipt or electronic receipt.

3. The system of claim 1, wherein the system is configured to print the nutritional tag alongside a relevant menu item on a printed menu.

4. The system of claim 2, wherein the system is further configured to cause the nutritional tag to be displayed in connection with a menu item on an electronic menu accessible by the consumer at the POS terminal.

* * * * *